United States Patent
Tam (10) Patent No.: US 10,161,878 B2
(45) Date of Patent: Dec. 25, 2018

(54) DIAMOND IDENTIFICATION APPARATUS

(71) Applicant: Jubilee Diamond Instrument (S) Pte. Ltd., Singapore (SG)

(72) Inventor: Kui Lim Tam, Singapore (SG)

(73) Assignee: Jubilee Diamond Instrument (S) Pte. Ltd., Singapore (SG)

(*) Notice: Subject to any disclaimer, the term of this patent is extended or adjusted under 35 U.S.C. 154(b) by 0 days.

(21) Appl. No.: 15/751,529

(22) PCT Filed: Jul. 7, 2016

(86) PCT No.: PCT/IB2016/054071
§ 371 (c)(1),
(2) Date: Feb. 9, 2018

(87) PCT Pub. No.: WO2017/025825
PCT Pub. Date: Feb. 16, 2017

(65) Prior Publication Data
US 2018/0238811 A1    Aug. 23, 2018

(30) Foreign Application Priority Data

Aug. 12, 2015 (SG) .......................... 10201506282W (51) Int. Cl.
*G01N 21/00* (2006.01)
*G01N 21/87* (2006.01)
(Continued)

(52) U.S. Cl.
CPC ................ *G01N 21/87* (2013.01); *G01J 1/16* (2013.01); *G01J 1/44* (2013.01)

(58) Field of Classification Search
CPC ... G01J 1/16; G01J 1/44; G01N 21/00; G01N 21/27; G01N 21/87; G01N 21/88; G01N 2201/126; G01B 11/24
See application file for complete search history.

(56) References Cited

U.S. PATENT DOCUMENTS 2,789,430 A    4/1957   Sinclaire
4,255,962 A    3/1981   Ashman
(Continued)

FOREIGN PATENT DOCUMENTS

WO    8001414       7/1980
WO    2015007873    1/2015
WO    2017208053    12/2017

OTHER PUBLICATIONS

Tam, Kui Lim; International Preliminary Report on Patentability for PCT/IB2016/054071, filed Jul. 7, 2016, dated Nov. 28, 2017, 4 pgs.
(Continued)

*Primary Examiner* — Abdullahi Nur
(74) *Attorney, Agent, or Firm* — Taylor English Duma LLP (57) ABSTRACT

A diamond identification apparatus is disclosed, the diamond identification apparatus comprising a support platform for receiving a gemstone at an observation position, a first light source arranged to emit light at a predetermined angle towards the observation position and a first photodiode arranged to detect an amount of light from the first light source being reflected from the gemstone at the observation position. The diamond identification apparatus further comprises a second light source arranged to emit light towards the observation position, a second photodiode arranged to detect light from the second light source that passes through the gemstone at the observation position and a processor unit.

16 Claims, 7 Drawing Sheets

(51) Int. Cl.
*G01J 1/16* (2006.01)
*G01J 1/44* (2006.01)

(56) References Cited

U.S. PATENT DOCUMENTS

| | | |
|---|---|---|
| 4,344,315 A | 8/1982 | Moxon et al. |
| 4,364,677 A | 12/1982 | Ashman |
| 4,394,580 A | 7/1983 | Gielisse |
| 4,488,821 A | 12/1984 | Wenckus |
| 5,801,819 A | 9/1998 | Spear et al. |
| 5,835,205 A | 11/1998 | Hunter et al. |
| 5,883,389 A | 3/1999 | Spear et al. |
| 5,955,735 A | 9/1999 | Coleman |
| 6,265,884 B1 | 7/2001 | Menashi |
| 6,439,766 B1 | 8/2002 | Nelson |
| 7,126,351 B2 | 10/2006 | Claus |
| 7,259,839 B2 | 8/2007 | Sivovolenko |
| 7,362,109 B2 | 4/2008 | Loginov |
| 7,382,445 B2 | 6/2008 | Sasian et al. |
| 8,278,906 B2 | 10/2012 | Loginov et al. |
| 8,564,316 B2 | 10/2013 | Kessler et al. |
| 8,749,253 B2 | 6/2014 | Kessler et al. |
| 9,395,350 B2 | 7/2016 | Kessler et al. |
| 2001/0023925 A1* | 9/2001 | Smith .............. G01N 21/87 250/372 |
| 2004/0008888 A1 | 1/2004 | Patton et al. |
| 2006/0044823 A1 | 3/2006 | Wong et al. |
| 2006/0087306 A1 | 4/2006 | Loginov |
| 2006/0098187 A1 | 5/2006 | Claus |
| 2012/0007619 A1 | 1/2012 | Zhu et al. |
| 2012/0059619 A1 | 3/2012 | Zhu et al. |
| 2012/0274751 A1 | 11/2012 | Smith et al. |
| 2014/0337035 A1 | 11/2014 | Kessler et al. |
| 2015/0219567 A1 | 8/2015 | Sim et al. |

OTHER PUBLICATIONS

Tam, Kui Lim; International Search Report and Written Opinion for PCT/IB2016/054071, filed Jul. 7, 2016, dated Oct. 26, 2016, 11 pgs.
Gems & Gemology; Article entitled: "Synthetic Moissanite: A New Diamond Substitute", published Winter 1997, 16 pgs.
Gems & Gemology; Symposium proceedings issue entitled: "Proceedings of the Third International Gemological Symposium", published Fall 1999, 185 pgs.
Tam, Kui Lim; International Search Report for PCT/IB2016/053208, filed Jun. 1, 2016, dated Feb. 28, 2017, 3 pgs.
Zeiss; Article entitled: "Education in Microscopy and Digital Imaging", published as early as Dec. 23, 2008, located at <https://web.archive.org/web/20081223034455/http://zeiss-campus.magnet.fsu.edu/articles/lightsources/tungstenhalogen.html>, 9 pgs.
Tam, Kui Lim; International Preliminary Report on Patentability for PCT/IB2016/053208, filed Jun. 1, 2016, dated Oct. 11, 2018, 7 pgs.

* cited by examiner

DIAMOND IDENTIFICATION APPARATUS

TECHNICAL FIELD

The following is in the field of gemology, and discloses an apparatus capable of determining whether a gemstone is a diamond and then determining whether the diamond is natural or possibly synthetic.

BACKGROUND ART

To the naked eye, it is sometimes difficult for the general public or even trained gemologists to determine whether a gemstone is a diamond or a diamond simulant (for example a synthetic moissanite or a cubic zirconia). Gemologists therefore rely on gemstone identification devices to identify the type of the gemstone. Some gemstone identification devices work on the principle of measuring the reflectivity of the gemstone. Each type of gemstone would reflect light in different amounts. Visible or infrared light is shown onto the gemstone and the amount of reflected light is measured by a photodetector or photodiode. The measured light is cross-referenced to a table or chart and the type of the gemstone is determined.

If the type of the gemstone is determined to be a diamond, the gemologist would then usually want to know if the diamond is natural or synthetic. Gemologists would usually use a detector device to shine ultraviolet light on the diamond. These detector devices work by measuring the permissibility of ultraviolet light through the diamond. If the diamond does not permit any ultraviolet light through, the diamond is inferred to be natural. If the diamond permits ultraviolet light through, there is a high possibility that the diamond is synthetic.

However, the two aforementioned devices usually exist as separate devices. This means that a gemologist would have to carry multiple devices around which can be very cumbersome. There does not exist in the art a single device that integrates the functionalities of the aforementioned devices in a portable and convenient manner.

Thus, there is a want for an apparatus or device which is capable of determining whether a gemstone is a diamond and then determining whether the diamond is natural or possibly synthetic.

Furthermore, other desirable features and characteristics will become apparent from the subsequent detailed description and the appended claims, taken in conjunction with the accompanying drawings and this background of the disclosure.

SUMMARY OF INVENTION

According to an aspect of the invention, a diamond identification apparatus is disclosed, the diamond identification apparatus comprising a support platform for receiving a gemstone at an observation position, a first light source arranged to emit light at a predetermined angle towards the observation position and a first photodiode arranged to detect an amount of light from the first light source being reflected from the gemstone at the observation position. The diamond identification apparatus further comprises a second light source arranged to emit light towards the observation position, a second photodiode arranged to detect light from the second light source that passes through the gemstone at the observation position and a processor unit. Wherein the processor unit is configured to determine that the gemstone is a diamond in response to the amount of light detected by the first photodiode, and if the gemstone is determined to be a diamond, then determine that the diamond is natural in response to the second photodiode not detecting light.

Preferably, the processor unit is further configured to determine that the diamond is possibly synthetic in response to the second photodiode detecting light.

Preferably, the processor unit determines that the gemstone is a diamond by calculating a reflectivity value in response to the amount of light detected by the first photodiode, and cross-referencing the reflectivity value with reference data.

Preferably, the reflectivity value is substantially 17.1%, or substantially 19%, or within the range of 17.1% and 19%.

Preferably, the second photodiode has a horizontal axis and a vertical axis, and wherein the first light source and the first photodiode are arranged such that the first light source and the first photodiode lie substantially along the horizontal axis of the second photodiode and sandwich the second photodiode, and the first light source and the first photodiode do not lie substantially along the vertical axis of the second photodiode.

Preferably, the first light source, the first photodiode and the second photodiode form part of a sensor module.

Preferably, the support platform defines an opening for receiving the gemstone at the observation position.

Preferably, the opening of the support platform and the second light source are arranged to lie substantially along the vertical axis of the second photodiode.

Preferably, the light emitted by the first light source is visible or infrared light.

Preferably, the light emitted by the second light source is ultraviolet light.

Preferably, the ultraviolet light emitted by the second light source has a wavelength of less than 370 nanometers.

Preferably, the first photodiode is oriented towards the observation position at substantially the predetermined angle.

Preferably, the predetermined angle is between 30° to 60°.

Preferably, the diamond identification apparatus further comprises a memory module and the memory module stores the reference data.

Preferably, the diamond identification apparatus further comprises a display module, and wherein the determination by the processor unit that the gemstone is a diamond, and the determination by the processor unit that the diamond is natural or possibly synthetic, are displayed on the display module.

Preferably, the diamond identification apparatus further comprises a housing for encapsulating the support platform, the first light source, the first photodiode, the second light source and the second photodiode, and the housing comprises a window which can be opened to insert or remove the gemstone.

According to another aspect of the invention, a sensor module for use in a diamond identification apparatus is described, the diamond identification apparatus comprising a processor unit, a support platform for receiving a gemstone at an observation position and a second light source arranged to emit light towards the observation position. The sensor module comprises a first light source arranged to emit light at a predetermined angle towards the observation position, a first photodiode arranged to detect an amount of light from the first light source being reflected from the gemstone at the observation position, and a second photodiode arranged to detect light from the second light source that passes through the gemstone at the observation position. Wherein the processor unit is configured to determine that the gemstone is a diamond in response to the amount of light detected by the first photodiode, and if the gemstone is determined to be a diamond, then determine that the diamond is natural in response to the second photodiode not detecting light.

Preferably, the second photodiode detects light and the processor unit determines that the diamond is possibly synthetic.

Preferably, the second photodiode has a horizontal axis and a vertical axis; and wherein the first light source and the first photodiode are arranged such that the first light source and the first photodiode lie substantially along the horizontal axis of the second photodiode and sandwich the second photodiode, and the first light source and the first photodiode do not lie substantially along the vertical axis of the second photodiode.

Preferably, the light emitted by the first light source is visible or infrared light.

Preferably, the first photodiode is oriented towards the observation position at substantially the predetermined angle.

Preferably, the predetermined angle is between 30° to 60°.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments, by way of example only, and to explain various principles and advantages in accordance with a present embodiment.

Skilled artisans will appreciate that elements in the figures are illustrated for simplicity and clarity and have not necessarily been depicted to scale. For example, the dimensions of some of the elements in the block diagrams or steps in the flowcharts may be exaggerated in respect to other elements to help improve understanding of the present embodiment.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the preferred embodiments to disclose an apparatus or device which is capable of determining whether a gemstone is a diamond and then determining whether the diamond is natural or possibly synthetic. These two steps usually occur in succession. Once a gemologist has determined that a gemstone is a diamond, logically, the gemologist would then want to know if the diamond is natural or possibly synthetic. Therefore, the disclosed apparatus is advantageous as it teaches a single apparatus capable of performing both these logically ensuing steps. Therefore, it is more convenient for the gemologist to carry around a single device with the combined functionalities as opposed to multiple devices.

Figure 1:
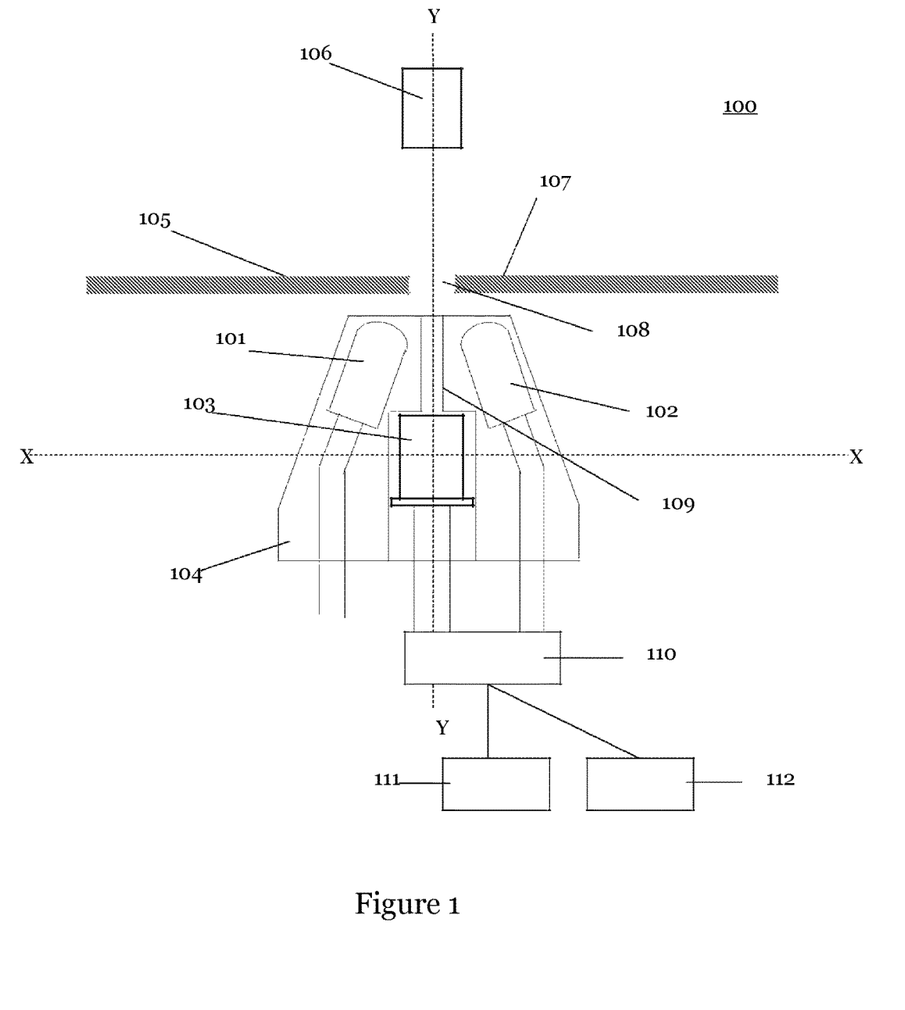
FIG. 1 shows a schematic diagram of an apparatus in accordance with an embodiment of the invention.

FIG. 1 shows a schematic diagram of apparatus 100 in accordance with an embodiment of the invention. Apparatus 100 comprises first light source 101, first photodiode 102 and second photodiode 103. Preferably, first light source 101, first photodiode 102 and second photodiode 103 form part of a sensor module 104.

Second photodiode 103 has a horizontal axis X-X and a vertical axis Y-Y. Preferably, the arrangement is such that first light source 101 and first photodiode 102 lie substantially along the horizontal axis X-X. Preferably, first light source 101 and first photodiode 102 sandwich second photodiode 103, such that second photodiode 103 lies intermediate between first light source 101 and first photodiode 102. In other words, first light source 101 lies on one side of vertical axis Y-Y while first photodiode 102 lies on the other side of vertical axis Y-Y. Preferably, first light source 101 and first photodiode 102 do not lie substantially along the vertical axis Y-Y as shown in FIG. 1. This is so that first light source 101 and first photodiode 102 do not obstruct any light which is to be detected by second photodiode 103.

Apparatus 100 further comprises support platform 105 and a second light source 106. Preferably, support platform 105 has a bank 107 which defines an opening 108. Preferably, opening 108 has a circular profile. Preferably, opening 108 has a width or diameter smaller than the table size of a gemstone. Preferably, opening 108 has a width or diameter of 1 millimeter (mm). When apparatus 100 is in operation, the gemstone is preferably placed on support platform 105. More particularly, the gemstone is preferably placed over opening 108, with portions of the gemstone contacting bank 107 for support. Preferably, the table portion of the gemstone is placed over opening 108 and rests on bank 107. This is the observation position of the gemstone. Preferably, opening 108 of support platform 105 lies substantially along vertical axis Y-Y of second photodiode 103.

Preferably, first light source 101 emits visible light or infrared light. Preferably, first light source 101 is arranged so as to emit light at a predetermined angle towards the observation position. Preferably, first light source 101 is orientated towards the observation position at a predetermined angle. Preferably, the predetermined angle is an acute angle between 30° to 60°. Preferably, the predetermined angle is substantially 45°. In operation, when the gemstone is placed at the observation position, the light from first light source 101 will reflect off the gemstone.

First photodiode 102 is arranged to detect the amount of visible light or infrared light emitted from first light source 101 being reflected from the gemstone placed at the observation position. Preferably, first photodiode 102 is a visible light or infrared light detector. Preferably, first photodiode 102 is arranged to be at the optimal position to detect the amount of visible light or infrared light emitted from first light source 101 being reflected from the gemstone placed at the observation position. Preferably, first photodiode 102 is arranged such that it is orientated towards the observation position. Preferably, first photodiode 102 is orientated towards the observation position at substantially the same predetermined angle as first light source 101.

Preferably, second light source 106 is arranged to be substantially perpendicular to support platform 105. Preferably, second light source 106 is arranged to be above support platform 105. Preferably, second light source 106 is arranged to lie substantially along vertical axis Y-Y of second photodiode 103. Preferably, second light source 106 emits ultraviolet light. Preferably, second light source 106 emits ultraviolet light with a wavelength of less than 370 nanometers (nm). Preferably, second light source 106 is arranged to emit ultraviolet light towards the observation position.

In operation, second photodiode 103 is arranged to detect the ultraviolet light emitted from second light source 106 that passes through the gemstone at the observation position. Preferably, second photodiode 103 is an ultraviolet light detector. Preferably, second photodiode 103 is substantially vertically aligned with second light source 106 and the gemstone at the observation position. As first light source 101 and first photodiode 102 are arranged to not lie substantially along vertical axis Y-Y of second photodiode 103, ultraviolet light emitted from second light source 106 can travel through gemstone at the observation position, and towards second photodiode 103 unobstructed. Preferably, second photodiode 103 is connected to vertical chamber 109 so that the ultraviolet light emitted from second light source 106 can be funneled unhindered towards second photodiode 103.

Apparatus 100 comprises processor unit 110. Preferably, processor unit 110 comprises a computer, a microcontroller, a microprocessor or a processor. Preferably, processor unit 110 can obtain readings from first photodiode 102 and second photodiode 103. Preferably, the readings from first photodiode 102 are the amount of detected reflected light. Preferably, the readings from second photodiode 103 are whether or not ultraviolet light has been detected. Preferably, apparatus 100 comprises the necessary electrical wiring between first photodiode 102, second photodiode 103 and processor unit 110 (as shown in FIG. 1). Preferably, processor unit 110 can send the necessary instructions to activate, deactivate and regulate first light source 101 and second light source 106.

Preferably, apparatus 100 comprises memory module 111 to store the readings from first photodiode 102 and second photodiode 103. Preferably, memory module 111 stores reference data. Preferably, the reference data contain a plurality of gemstone types and their corresponding reflectivity values.

Preferably, apparatus 100 comprises display module 112. Preferably, display module 112 can comprise a liquid crystal display (LCD). Preferably, processor unit 110 can display on display module 112 the results of the determination e.g. that the gemstone is a diamond, that the diamond is natural or that the diamond is possibly synthetic. Preferably, display module 112 has touch screen capability and can accept user input.

Preferably, apparatus 100 comprises a power supply module (not shown in FIG. 1) to provide power to first light source 101, second light source 106, first photodiode 102, second photodiode 103, processing unit 110, memory module 111 and display module 112.

Preferably, apparatus 100 also has a housing (not shown in FIG. 1) which substantially encapsulates support platform 105, first light source 101, second light source 106, first photodiode 102 and second photodiode 103. Preferably, the housing has a window which can be opened to insert or remove the gemstone. Preferably, the housing has buttons which can trigger processor unit 110 to execute actions.

Figure 2:
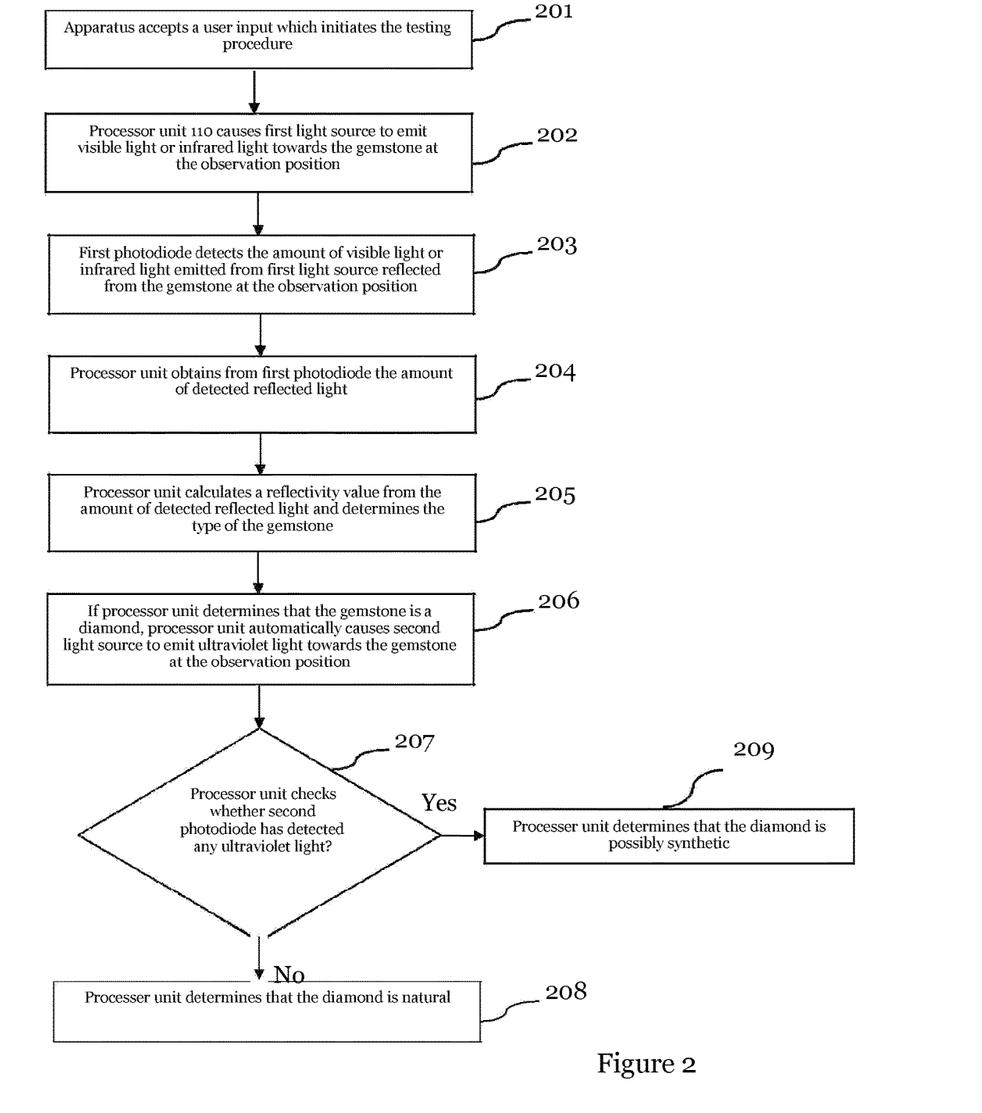
FIG. 2 shows a flowchart depicting the steps taken by an apparatus to determine the type of the gemstone and if the type of the gemstone is determined to be diamond, then determine whether the diamond is natural or possibly synthetic, in accordance with an embodiment of the invention.
Figure 3:
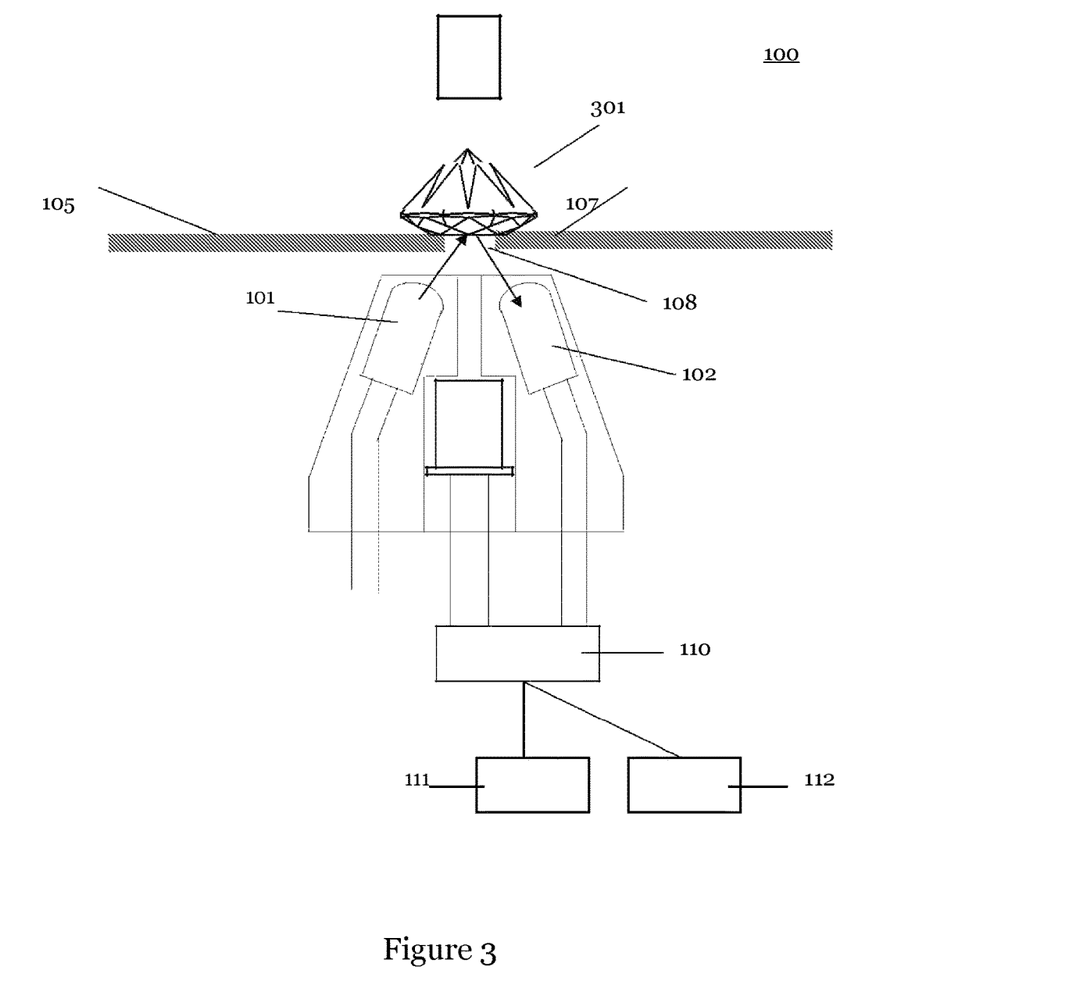
FIG. 3 shows a schematic diagram of an apparatus in operation to determine the type of a gemstone, in accordance with an embodiment of the invention.

FIG. 2 shows a flowchart depicting the steps taken by apparatus 100 to determine the type of the gemstone and if the type of the gemstone is determined to be diamond, then determine whether the diamond is natural or possibly synthetic, in accordance with an embodiment of the invention. FIG. 3 shows a schematic diagram of apparatus 100 in operation to determine the type of the gemstone, in accordance with an embodiment of the invention. Gemstone 301 is placed at the observation position on support platform 105. Preferably, the table portion of gemstone 301 is placed over opening 108 and rests on bank 107. (see FIG. 3). This orientation of gemstone 301 is ideal as the table portion of gemstone 301 is substantially flat, which optimizes the reflection of light (from first light source 101) off gemstone 301 and onto first photodiode 102. Preferably, gemstone 301 is colorless. Preferably, gemstone 301 is a colorless diamond graded from D to J.

Now referring to FIG. 2, in step 201, apparatus 100 accepts a user input which initiates the testing procedure. This user input may be via a button on the housing of apparatus 100 that is depressed or via a touch screen input on display module 112.

In step 202, processor unit 110 causes first light source 101 to emit visible light or infrared light towards gemstone 301 at the observation position. This is illustrated in FIG. 3.

In step 203, first photodiode 102 detects the amount of visible light or infrared light emitted from first light source 101 reflected from gemstone 301 at the observation position. This is illustrated in FIG. 3.

In step 204, processor unit 110 obtains from first photodiode 102 the amount of detected reflected light.

In step 205, processor unit 110 calculates a reflectivity value from the amount of detected reflected light and determines the type of gemstone 301. The reflectivity value represents the percentage of light being reflected. A particular type of gemstone would exhibit a range of reflectivity values. For example, diamond would normally exhibit reflectivity values of between 17.1% and 19%. Preferably, the different types of gemstones and their corresponding reflectivity values will be stored as reference data in memory module 111. Therefore, once the reflectivity value has been calculated, processor unit 110 would cross-reference the calculated reflectivity value with the reference data to determine the type of gemstone 301. An exemplary method to cross-reference the calculated reflectivity value with the reference data to determine the type of gemstone 301 is illustrated in FIG. 4.

Figure 4:
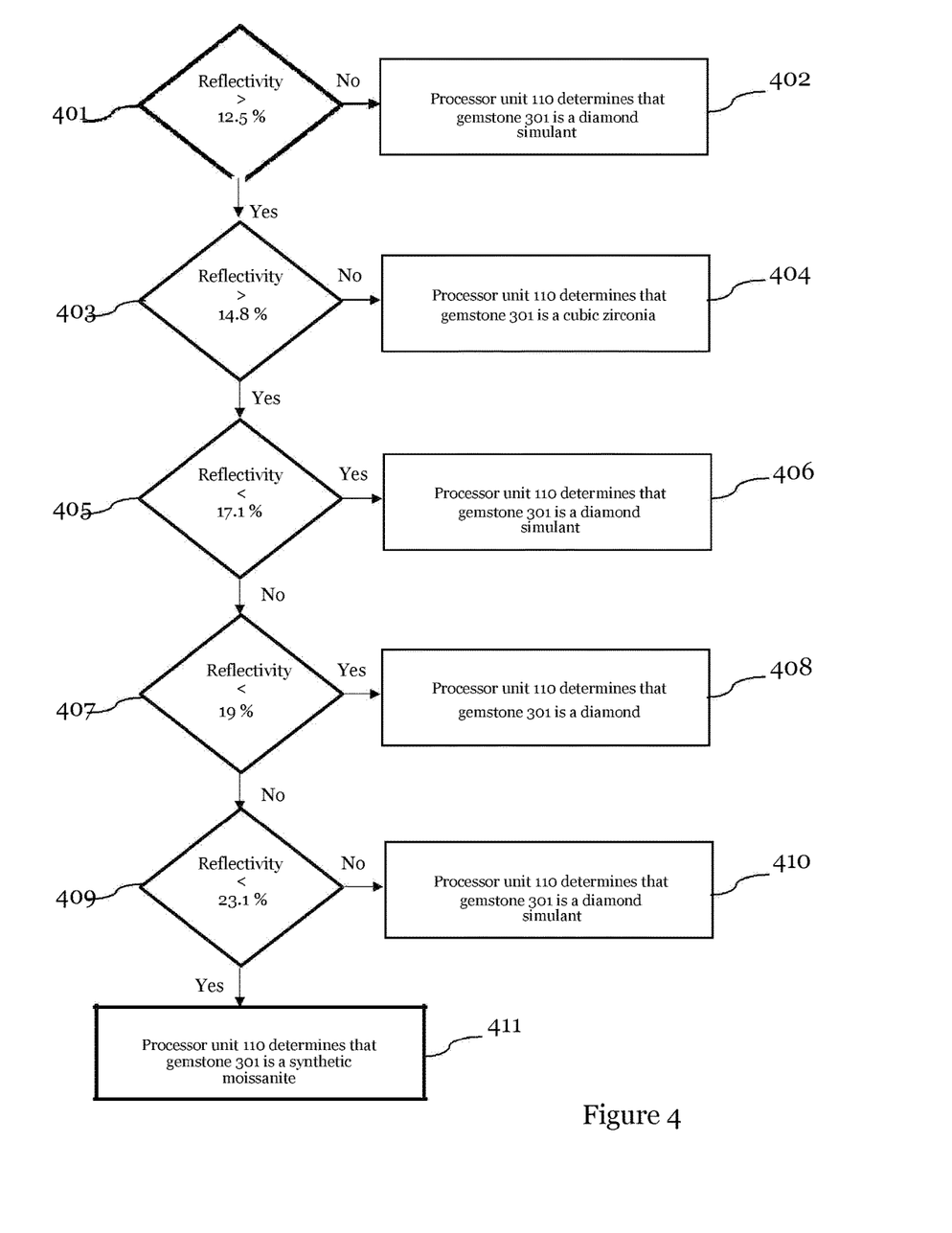
FIG. 4 illustrates an exemplary method to cross-reference the calculated reflectivity value with the reference data to determine the type of the gemstone.

Referring to FIG. 4, processor unit 110 first checks if the reflectivity value is larger than 12.5% 401. If the reflectivity value is smaller than 12.5%, processing unit 110 determines that gemstone 301 is a diamond simulant 402. If the reflectivity value is larger than 12.5%, processor unit 110 then checks to see if the reflectivity value is larger than 14.8% 403. If the reflectivity value is smaller than 14.8%, processor unit 110 determines that gemstone 301 is a cubic zirconia 404. If the reflectivity value is larger than 14.8%, processor unit 110 then checks to see if the reflectivity value is smaller than 17.1% 405. If the reflectivity value is smaller than 17.1%, processor unit 110 determines that gemstone 301 is a diamond simulant 406. If reflectivity value is larger than 17.1%, processor unit 110 then checks to see if the reflectivity value is smaller than 19% 407. If the reflectivity value is smaller than 19%, processor unit 110 determines that gemstone 301 is a diamond 408. If the reflectivity value is larger than 19%, processor unit 110 checks to see if the reflectivity value is smaller than 23.1% 409. If the reflectivity value is smaller than 23.1%, processor unit 110 determines that gemstone 301 is a synthetic moissanite 411. If the reflectivity value is larger than 23.1%, processor unit 110 determines that gemstone 301 is a diamond simulant 410. Preferably, processor unit 110 can display on display module 112 the results of the determination. Alternatively, the type of gemstone 301 can be determined by the refractive index. A particular type of gemstone 301 would exhibit a specific refractive index. Preferably, the refractive index can be calculated from the reflectivity value using the equation $x=[(n-1)/(n+1)]^2$, where x is the reflectivity value and n is the refractive index.

Figure 5:
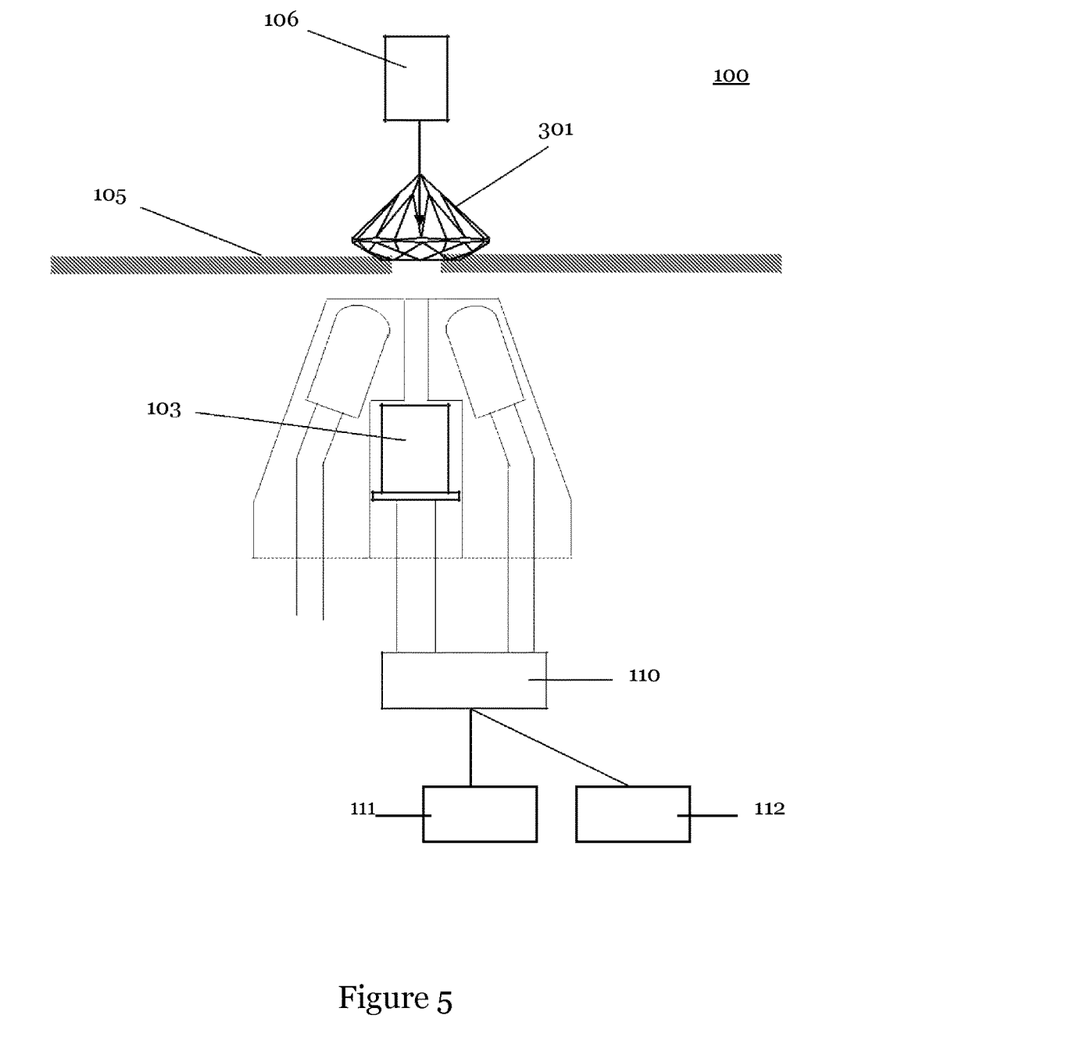
FIG. 5 shows a schematic diagram of an apparatus in operation to determine if the diamond is natural or possibly synthetic, in accordance with an embodiment of the invention.

Referring back to FIG. 2, in step 206, if processor unit 110 determines that gemstone 301 is a diamond, processor unit 110 automatically causes second light source 106 to emit ultraviolet light towards gemstone 301 at the observation position. This is illustrated in FIG. 5. Preferably, processor unit 110 displays on display module 112 the results of the determination i.e. that the gemstone is a diamond.

In step 207, processor unit 110 checks whether second photodiode 103 has detected any ultraviolet light.

If second photodiode 103 has not detected any ultraviolet light (i.e. gemstone 301 at the observation position did not allow any ultraviolet light through and onto second photodiode 103), in step 208, processor unit 110 determines that gemstone/diamond 301 is natural. Preferably, processor unit 110 displays on display module 112 the results of the determination i.e. that the diamond is natural.

If second photodiode 103 has detected ultraviolet light (i.e. gemstone 301 at the observation position has allowed ultraviolet light through and onto second photodiode 103), in step 209, processor unit 110 determines that gemstone/diamond 301 is possibly synthetic. The reason why it is not possible to definitively determine that diamond 301 is synthetic via this test is due to HPHT-enhanced diamonds and a few natural 'Type' diamonds. HPHT-enhanced diamonds are diamonds which undergo a High Pressure High Temperature (HPHT) process. The HPHT process will change the color of the diamonds, for example from brownish diamonds to colorless diamonds, or from faint yellow diamonds to yellow fancy diamonds. Despite the change in color, HPHT-enhanced diamonds allow ultraviolet light through as the HPHT-enhanced diamond is natural. Besides that, all Type II natural diamonds and very rare Type IaB natural diamonds also allow ultraviolet light to pass through. The amount of Type II natural diamonds and Type IaB is very low around 2%. For this reason, the fact that diamond 301 allows ultraviolet light through (such that second photodiode 103 detects it) does not definitively conclude that diamond 301 is synthetic. Preferably, processor unit 110 displays on display module 112 the results of the determination i.e. that the diamond is possibly synthetic.

Figure 6:
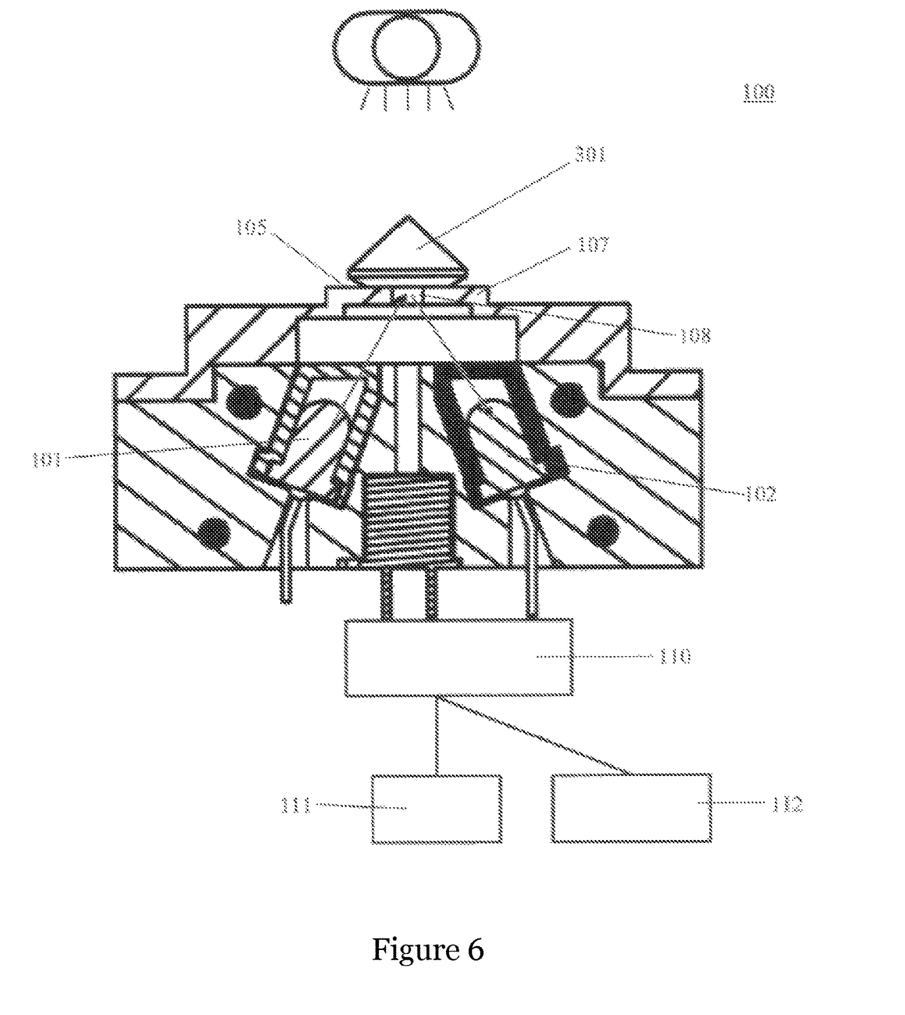
FIG. 6 shows a further embodiment, which is similar to the embodiment of FIG. 3.
Figure 7:
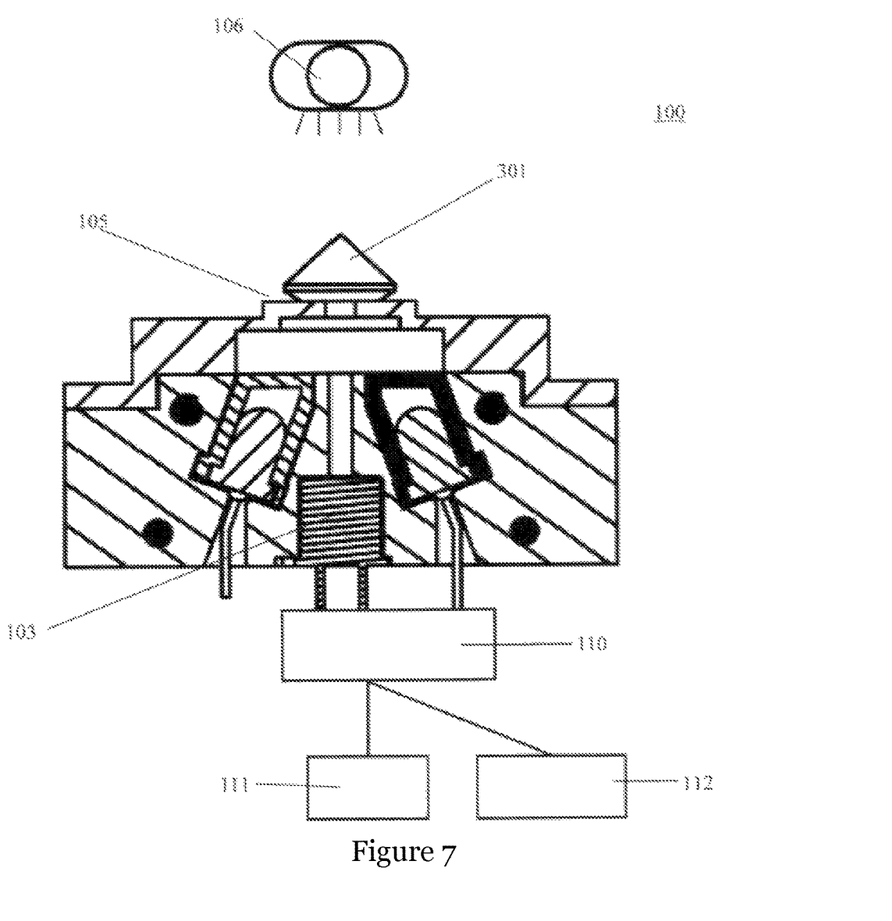
FIG. 7 shows a further embodiment, which is similar to the embodiment of FIG. 5.

FIG. 6 shows a further embodiment, which is similar to the embodiment of FIG. 3 and FIG. 7 shows a further embodiment, which is similar to the embodiment of FIG. 5. For the sake of brevity, the description of FIGS. 3 and 5 is not repeated here.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

The embodiments can also be described with the following lists of elements being organized into items. The respective combinations of features which are disclosed in the item list are regarded as independent subject matter, respectively, that can also be combined with other features of the application.

1. A diamond identification apparatus comprising:
   a support platform for receiving a gemstone at an observation position;
   a first light source arranged to emit light at a predetermined angle towards the observation position;
   a first photodiode arranged to detect an amount of light from the first light source being reflected from the gemstone at the observation position;
   a second light source arranged to emit light towards the observation position;
   a second photodiode arranged to detect light from the second light source that passes through the gemstone at the observation position; and
   a processor unit;
   wherein the processor unit is configured to:
   determine that the gemstone is a diamond in response to the amount of light detected by the first photodiode;
   and if the gemstone is determined to be a diamond, then determine that the diamond is natural in response to the second photodiode not detecting light.

2. The diamond identification apparatus of item 1 wherein the processor unit is further configured to determine that the diamond is possibly synthetic in response to the second photodiode detecting light.

3. The diamond identification apparatus of item 1 or item 2, wherein the processor unit determines that the gemstone is a diamond by calculating a reflectivity value in response to the amount of light detected by the first photodiode, and cross-referencing the reflectivity value with reference data.

4. The diamond identification apparatus of item 3, wherein the reflectivity value is substantially 17.1%, or substantially 19%, or within the range of 17.1% and 19%.

5. The diamond identification apparatus of any one of the preceding items wherein the second photodiode has a horizontal axis and a vertical axis; and wherein the first light source and the first photodiode are arranged such that:
   the first light source and the first photodiode lie substantially along the horizontal axis of the second photodiode and sandwich the second photodiode; and
   the first light source and the first photodiode do not lie substantially along the vertical axis of the second photodiode.

6. The diamond identification apparatus of any one of the preceding items wherein the first light source, the first photodiode and the second photodiode form part of a sensor module.

7. The diamond identification apparatus of any one of the preceding items wherein the support platform defines an opening for receiving the gemstone at the observation position.

8. The diamond identification apparatus of item 7 wherein the opening of the support platform and the second light source are arranged to lie substantially along the vertical axis of the second photodiode.

9. The diamond identification apparatus of any one of the preceding items wherein the light emitted by the first light source is visible or infrared light.

10. The diamond identification apparatus of any one of the preceding items wherein the light emitted by the second light source is ultraviolet light.

11. The diamond identification apparatus of item 10 wherein the ultraviolet light emitted by the second light source has a wavelength of less than 370 nanometers.

12. The diamond identification apparatus of any one of the preceding items wherein the first photodiode is oriented towards the observation position at substantially the predetermined angle.

13. The diamond identification apparatus of any one of the preceding items wherein the predetermined angle is between 30° to 60°.

14. The diamond identification apparatus of any one of items 3 to 13 further comprising a memory module and wherein the memory module stores the reference data.

15. The diamond identification apparatus of any one of items 2 to 14 further comprising a display module, and wherein the determination by the processor unit that the gemstone is a diamond, and the determination by the processor unit that the diamond is natural or possibly synthetic, are displayed on the display module.

16. The diamond identification apparatus of any one of the preceding items further comprising a housing for encapsulating the support platform, the first light source, the first photodiode, the second light source and the second photodiode; the housing comprising a window which can be opened to insert or remove the gemstone.

17. A sensor module for use in a diamond identification apparatus, the diamond identification apparatus comprising a processor unit, a support platform for receiving a gemstone at an observation position and a second light source arranged to emit light towards the observation position, the sensor module comprising:
    a first light source arranged to emit light at a predetermined angle towards the observation position;
    a first photodiode arranged to detect an amount of light from the first light source being reflected from the gemstone at the observation position; and
    a second photodiode arranged to detect light from the second light source that passes through the gemstone at the observation position;
    wherein the processor unit is configured to:
        determine that the gemstone is a diamond in response to the amount of light detected by the first photodiode;
        and if the gemstone is determined to be a diamond, then determine that the diamond is natural in response to the second photodiode not detecting light.

18. The sensor module of item 17 wherein the second photodiode detects light and the processor unit determines that the diamond is possibly synthetic.

19. The sensor module of item 17 or item 18 wherein the second photodiode has a horizontal axis and a vertical axis; and wherein the first light source and the first photodiode are arranged such that:
    the first light source and the first photodiode lie substantially along the horizontal axis of the second photodiode and sandwich the second photodiode; and
    the first light source and the first photodiode do not lie substantially along the vertical axis of the second photodiode.

20. The sensor module of any one of items 17 to 19 wherein the light emitted by the first light source is visible or infrared light.

21. The sensor module of any one of items 17 to 20 wherein the first photodiode is oriented towards the observation position at substantially the predetermined angle.

22. The sensor module of any one of items 17 to 21 wherein the predetermined angle is between 30° to 60°.

The invention claimed is:

1. A diamond identification apparatus comprising:
    a support platform for receiving a gemstone at an observation position;
    a first light source arranged to emit infrared light at a predetermined angle towards the observation position;
    a first photodiode arranged to detect an amount of the infrared light from the first light source being reflected from the gemstone at the observation position;
    a second light source arranged to emit ultraviolet light towards the observation position;
    a second photodiode arranged to detect a presence of the ultraviolet light from the second light source that passes through the gemstone at the observation position; and
    a processor unit;
    wherein the processor unit is configured to:
        determine whether the gemstone is a diamond in response to the amount of the infrared light detected by the first photodiode; and
        if the gemstone is determined to be a diamond, then determine whether the diamond is natural in response to the second photodiode not detecting the presence of the ultraviolet light,
    wherein the processor unit determines that the gemstone is a diamond by calculating a reflectivity value in response to the amount of the infrared light detected by the first photodiode, and cross-referencing the reflectivity value with reference data.

2. The diamond identification apparatus of claim 1, wherein the processor unit is further configured to determine that the diamond is possibly synthetic in response to the second photodiode detecting the presence of the ultraviolet light.

3. The diamond identification apparatus of claim 1, wherein the reflectivity value is 17.1%, or 19%, or within the range of 17.1% and 19%.

4. The diamond identification apparatus of claim 1, wherein the second photodiode has a horizontal axis and a vertical axis; and wherein the first light source and the first photodiode are arranged such that:
    the first light source and the first photodiode lie along the horizontal axis of the second photodiode and sandwich the second photodiode; and
    the first light source and the first photodiode do not lie along the vertical axis of the second photodiode.

5. The diamond identification apparatus of claim 1, wherein the first light source, the first photodiode and the second photodiode form part of a sensor module.

6. The diamond identification apparatus of claim 1, wherein the support platform defines an opening for receiving the gemstone at the observation position.

7. The diamond identification apparatus of claim 6, wherein the opening of the support platform and the second light source are arranged to lie along the vertical axis of the second photodiode.

8. The diamond identification apparatus of claim 1, wherein the ultraviolet light emitted by the second light source has a wavelength of less than 370 nanometers.

9. The diamond identification apparatus of claim 1, wherein the first photodiode is oriented towards the observation position at the predetermined angle.

10. The diamond identification apparatus of claim 1, wherein the predetermined angle is between 30° to 60°.

11. The diamond identification apparatus of claim 3, further comprising a memory module and wherein the memory module stores the reference data.

12. The diamond identification apparatus of claim 2, further comprising a display module, and wherein the determination by the processor unit that the gemstone is a diamond, and the determination by the processor unit that the diamond is natural or possibly synthetic, are displayed on the display module.

13. A sensor module for use in a diamond identification apparatus, the sensor module comprising:
- a first light source arranged to emit infrared light at a predetermined angle towards an observation position that is provided for receiving a gemstone;
- a first photodiode arranged to detect an amount of the infrared light from the first light source being reflected from the gemstone at the observation position, and for sending readings of said amount to a processor unit of the diamond identification apparatus;
- a second light source arranged to emit ultraviolet light towards the observation position; and
- a second photodiode arranged to detect a presence of the ultraviolet light from the second light source that passes through the gemstone at the observation position, and for sending readings of said presence to the processor unit of the diamond identification apparatus.

14. The sensor module of claim 13, wherein the second photodiode has a horizontal axis and a vertical axis; and wherein the first light source and the first photodiode are arranged such that:
- the first light source and the first photodiode lie along the horizontal axis of the second photodiode and sandwich the second photodiode; and
- the first light source and the first photodiode do not lie along the vertical axis of the second photodiode.

15. The sensor module of claim 13, wherein the first photodiode is oriented towards the observation position at the predetermined angle.

16. The sensor module of claim 13, wherein the predetermined angle is between 30° to 60°.

* * * * *